(12) United States Patent
Akizumi et al.

(10) Patent No.: US 10,758,457 B2
(45) Date of Patent: Sep. 1, 2020

(54) CURABLE COMPOSITION AND DENTAL FILLING RESTORATIVE MATERIAL

(71) Applicant: TOKUYAMA DENTAL CORPORATION, Tokyo (JP)

(72) Inventors: Hironobu Akizumi, Tokyo (JP); Chika Toriyabe, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 5 days.

(21) Appl. No.: 15/769,234

(22) PCT Filed: Oct. 21, 2016

(86) PCT No.: PCT/JP2016/081367
§ 371 (c)(1),
(2) Date: Apr. 18, 2018

(87) PCT Pub. No.: WO2017/069274
PCT Pub. Date: Apr. 27, 2017

(65) Prior Publication Data
US 2018/0303721 A1 Oct. 25, 2018

(30) Foreign Application Priority Data
Oct. 21, 2015 (JP) ................. 2015-207053

(51) Int. Cl.
| | | |
|---|---|---|
| A61K 6/08 | (2006.01) | |
| A61K 6/54 | (2020.01) | |
| A61K 6/853 | (2020.01) | |
| A61K 6/884 | (2020.01) | |
| A61K 6/887 | (2020.01) | |
| C08L 33/08 | (2006.01) | |
| A61K 6/16 | (2020.01) | |
| C08F 20/18 | (2006.01) | |

(52) U.S. Cl.
CPC ............ *A61K 6/54* (2020.01); *A61K 6/853* (2020.01); *A61K 6/884* (2020.01); *A61K 6/887* (2020.01); *C08L 33/08* (2013.01); *A61K 6/16* (2020.01); *C08F 20/18* (2013.01); *C08L 2203/02* (2013.01)

(58) Field of Classification Search
CPC ....... A61K 6/0002; A61K 6/0005; A61K 6/16
See application file for complete search history.

(56) References Cited

U.S. PATENT DOCUMENTS

| | | |
|---|---|---|
| 8,993,650 B2 | 3/2015 | Uchida et al. |
| 2008/0319104 A1 | 12/2008 | Klapdohr et al. |
| 2010/0081728 A1 | 4/2010 | Uchida et al. |
| 2013/0096226 A1* | 4/2013 | Toriyabe .............. A61K 6/0091 523/115 |
| 2014/0206792 A1 | 7/2014 | Ishizaka et al. |
| 2016/0008232 A1 | 1/2016 | Toriyabe et al. |
| 2017/0049665 A1 | 2/2017 | Kita et al. |

FOREIGN PATENT DOCUMENTS

| | | |
|---|---|---|
| CN | 102905673 A | 1/2013 |
| JP | S60-011505 A | 1/1985 |
| JP | S62-086003 A | 4/1987 |
| JP | S63-218703 A | 9/1988 |
| JP | 2001-239661 A | 9/2001 |
| JP | 2004-276492 A | 10/2004 |
| JP | 2007-532518 A | 11/2007 |
| JP | 2010083833 A | 4/2010 |
| JP | 2010-215694 A | 9/2010 |
| JP | 2012-153640 A | 8/2012 |
| RU | 2472708 C2 | 1/2013 |
| WO | 2010045105 A1 | 4/2010 |
| WO | 2011/158742 A1 | 12/2011 |
| WO | 2012/176877 A1 | 12/2012 |
| WO | 2014/148293 A1 | 9/2014 |
| WO | 2015/125470 A1 | 8/2015 |
| WO | 2015/141683 A1 | 9/2015 |

OTHER PUBLICATIONS

Korean Office Action issued in Korea Patent Application No. 10-2018-7007737; dated Jul. 5, 2018 (4 pages).
Office Action issued in Chinese Application No. 201680061397.2, dated Nov. 16, 2018 (14 pages).
International Search Report issued in PCT/JP2016/081367 dated Dec. 27, 2016 (2 pages).
Written Opinion of the International Searching Authority issued in PCT/JP2016/081367 dated Dec. 27, 2016 (3 pages).
International Preliminary Report on Patentability from PCT/JP2016/081367 dated Jun. 20, 2017 (11 pages).
Shinoda, Hiroyuki and Fujieda, Ichiro, "Shikisai Kogaku Nyumon", Morikita Publishing Co., Ltd., 1st print published on May 1, 2007, pp. 73-78 (10 pages) w/partial translation.
Saito, Katsuhiro, et al., "Hikari to Shikisai no Kagaku", Kodansha, Ltd., 1st print published on Oct. 20, 2010, pp. 118-139 (21 pages) w/partial translation.
The Color Science Association of Japan, ed., "Handbook of Color Science (3rd Edition)", University of Tokyo Press, published in Apr. 2011, pp. 1130-1181 (35 pages) w/partial translation.
JIS Z8102, Z8110: 2001, Japanese Industrial Standard, "Names of non-luminous object colours", (16 pages) w/partial ranslation.
Matsumura, Hideo and Tagami, Junji, rev., "Adhesion Yearbook 2006", 1st Edition, Quintessence Publishing Co., Ltd., published in Aug. 2006, pp. 129-137 (14 pages) w/partial translation.

(Continued)

*Primary Examiner* — Michael F Pepitone
(74) *Attorney, Agent, or Firm* — Osha Liang LLP

(57) ABSTRACT

Provided is a curable composition including a polymerizable monomer component (A), a spherical filler (B) having an average particle size within the range of 230-1000 nm, and a polymerization initiator (C), wherein the curable composition is characterized by having a value (V) of less than 5 and a chroma (C) of 0.05 or higher in colorimetric values according to the Munsell Color System in colored light on a black background, and a value (V) of 6 or higher and a chroma (C) of less than 2 in colorimetric values according to the Munsell Color System in colored light on a white background, each of the values (V) and chroma (C) being measured using a color difference meter in a state in which a 1-mm-thick cured article has been formed.

6 Claims, No Drawings

(56) References Cited

OTHER PUBLICATIONS

Miyazaki, Masashi, "Science & Technique of Composite Resin Restoration", 1st Edition, Quintessence Publishing Co., Ltd., published in Jan. 2010, pp. 48-49 (6 pages) w/partial translation.
Office Action issued in corresponding Russian Application No. 2018116597; dated Nov. 26, 2019 (15 pages).
Pre-grant Opposition filed by Dentscare LTDA in corresponding Brazilian Application No. 112018006772-5, dated Apr. 6, 2020 (39 pages).

* cited by examiner

CURABLE COMPOSITION AND DENTAL FILLING RESTORATIVE MATERIAL

CROSS-REFERENCE TO RELATED APPLICATIONS

This application is a National Stage of International Application No. PCT/JP2016/081367, filed on Oct. 21, 2016, which claims priority to Japanese Patent Application No. 2015-207053, filed on Oct. 21, 2015. The contents of the priority applications are incorporated by reference in their entirety.

TECHNICAL FIELD

The present invention relates to a curable composition, and more particularly, to a curable composition which is useful for applications such as a dental material, an ink, a film, and a construction material, and above all, which is useful as a dental material. More specifically, the invention relates to a curable composition that can have the external appearance color tone well-controlled without using a dye or a pigment, and exhibits reduced decoloration or discoloration, and particularly to a curable composition useful as a dental filling restorative material that provides excellent convenience and esthetics.

BACKGROUND ART

In a variety of fields such as dental materials, recording materials, and construction materials, curable compositions including polymerizable monomers and inorganic or organic fillers have been conventionally used. Particularly in the field of dental filling restorative materials, since curable compositions can impart a color tone equivalent to that of natural teeth color and is easily operable, curable compositions have been rapidly popularized as materials for restoring teeth that have been damaged by dental caries, fracture, and the like. In recent years, from the viewpoint of enhancing the mechanical strength or enhancing the adhesive force to teeth, curable compositions are also used for the restoration of anterior teeth as well as for molar teeth to which high occlusal pressure is exerted. For example, Patent Document 1 discloses a composite composition for photopolymerization having excellent depth of cure, the composition including a polymerizable vinyl monomer; an inorganic oxide having a refractive index that is lower than the refractive index of a polymer of the vinyl monomer and including particles having a particle size of 0.1 µm to 1.0 µm; and a catalyst capable of initiating photopolymerization by visible light. Furthermore, Patent Document 2 discloses a composite composition for photopolymerization having excellent depth of cure, from which a cured material having an adequate degree of translucency is obtained, the composition including a polymerizable vinyl monomer; a filler having a refractive index that is higher than the refractive index of a polymer of the vinyl monomer; a filler having a refractive index that is lower than the refractive index of the relevant polymer; and a catalyst capable of initiating photopolymerization by visible light.

For the color tone adjustment of conventional curable compositions such as the compositions of Patent Documents 1 and 2, pigment substances, dye substances, and the like have been used, and various color tones have been prepared by varying the mixing ratios of pigment substances, dye substances, and the like, which have different color tones. However, coloration by means of pigment substances and dye substances tends to undergo decoloration or discoloration caused by aged deterioration. In regard to dental filling restorative materials, a curable composition including pigment substances, dye substances, and the like exhibit high color tone adaptability immediately after restoration; however, after restoration, the curable composition is discolored as time elapses, and a phenomenon that the external appearance of the restored site becomes incompatible with the appearance of natural teeth, occurs in many cases.

In this regard, as a structure that can be colored without using a pigment substance, a dye substance, or the like, it has been known that structural color that is expressed by, for example, interference, diffraction, refraction, or scattering or light may be utilized. Generally, color (expression of color) of a material is such that when light having a certain wavelength is absorbed, light of other wavelengths is reflected or transmitted, and when the reflected light has a wavelength in the visible light range, this light is perceived as color. This coloring (hue) is generally color developed by a natural or artificial dye or pigment, and is coloring resulting from energy exchange between light and an object. On the other hand, there is color that is not based on a dye or a pigment but is expressed only by means of the physical nature of light, without exchange of light energy. This is structural color. A synonym for this is "interference color"; however, the interference color is a kind of structural color. The structural color is expressed by diffraction, refraction, interference, scattering, or the like of light. For example, the structural color is expressed in thin film interference caused by coating of spectacles or the like, multilayer film interference caused by a multilayer configuration of thin films, diffraction grating, and a photonic crystal. These have regular structures having constant intervals; however, the structural color is also expressed by scattering caused by, for example, fine particles dispersed in a matrix, which is not a regular structure (all, regarding the structural color, see Non-Patent Documents 1 to 4). For example, Patent Document 3 discloses a recorded matter expressing colored light by means of light interference, the recorded matter having sites where solid fine particles aggregate and arrange on a liquid-repellent surface of a material to be recorded and form a regular periodic structure, in which the standard color chart value of the liquid-repellent surface is 6 or less, and the recorded matter has black color or a dark color having a chroma of 8 or less. Patent Document 4 discloses a color sheet that does not use a coloring dye or pigment and visually presents a chromatic color as a structural color, in which organic or inorganic spherical particles having black color or an achromatic color and having an average particle size (d) in the range of 100 nm to 500 nm as represented on a volume basis, are regularly aligned on a color-developing base material sheet and form a particulate laminate thereon. Coloring by a structural color that utilizes such interference, diffraction, refraction, scattering or the like of light has an advantage that a phenomenon of decoloration or discoloration appearing in the case of using a pigment substance, a dye substance or the like is not observed.

In recent years, in the field of dental filling restorative materials, there is an increasing demand not only for the recovery of occlusion but also for esthetic restoration of the appearance looking like natural teeth. There is a demand for a restorative material which can reproduce not only simple equivalent color tones but also the transparency or color tone at various restoration sites of teeth, and which undergoes less aged deterioration. From this point of view, in both of the compositions of Patent Documents 1 and 2, the particle size distribution of the filler or the relation between the refractive indices of the polymer as a matrix and the filler were not optimized, coloring by a structural color was not always obtained, and since the compositions were colored using a pigment or the like, a phenomenon of decoloration or discoloration caused by aged deterioration occurred.

Thus, Patent Document 5 discloses a curable dental material having high esthetic properties and exhibiting adjustable translucency and high opalescence, the curable dental material containing a monomer having a refractive index of lower than 1.45, an opalescent filler having a refractive index of lower than 1.45, another conventional filler or filler mixture, and at least one selected from the group consisting of a polymerization initiator, a stabilizer, and a colorant, in which the difference between the refractive index of the monomer and the refractive index of the opalescent filler is less than or equal to 0.04, and the average particle size of the opalescent filler is 230 nm±50 nm. However, in the material of Patent Document 5, since the relation between the refractive index of a polymer of the monomer and the refractive index of the opalescent filler is not optimized, coloring by a structural color is not necessarily sufficient, and the range of the average particle size is limited to a range that exhibits opalescence. Thus, it was difficult to reproduce the transparency or color tone at various restoration sites of teeth.

Patent Document 6 discloses a dental composite restorative material which exhibits an opal effect (the same unique light scattering phenomenon as that of mineral opal) and provides excellent esthetic properties, the dental composite restorative material including (A) a polymerizable monomer; (B) spherical silica-based particles having an average particle size in the range of 0.1 μm to 0.5 μm and a standard deviation of the particle size distribution of 1.30 or less; (C) an organic-inorganic composite filler obtained by dispersing these silica-based particles in an organic resin matrix; and (D) a polymerization initiator, in which the difference between the refractive indices of the spherical silica-based particles and a polymer of the polymerizable monomer is 0.1 or less, and the difference between the refractive indices of the organic inorganic composite filler and a polymer of the polymerizable monomer is 0.1 or less. However, in regard to Patent Document 6, the occasion of obtaining an opal effect is substantially limited to a case in which the refractive index of the polymer is larger than the refractive indices of the spherical silica-based particles and the organic-inorganic composite filler, and the opal effect exhibits a bluish color. A bluish-colored dental composite restorative material is suitable for the restoration of an incisal part of a tooth; however, this material is not necessarily suitable particularly for the restoration of the tooth cervix, where reproduction of the hue of the yellowish to reddish dentinal color is necessary. As such, in regard to the material of Patent Document 6, since the relation between the refractive indices of the polymer and the filler is not optimized, it is difficult to reproduce the color tones of various restoration sites of teeth.

As explained above, it is required for a composite restorative material that the color tones of teeth at various treated sites are exactly reproduced. The crown part of a natural tooth is formed from dentine and enamel, and the color tone (hue, chroma, and value) varies from site to site. For example, since an incisal part has a thin dentinal layer and is almost covered with enamel, the incisal part is highly transparent and exhibits a bluish hue. In contrast, the tooth cervix is opaque because the deep part has a thick dentinal layer, and compared to an incisal part, the tooth cervix has high value (lightness or darkness of a color) and high chroma (vividness of color) and has the yellowish to reddish hue of the dentinal color. That is, the chroma and value decrease in the direction from the tooth cervix having a thick dentinal layer at the deep part, toward the incisal part having a thin dentinal layer. Furthermore, the incisal part, which is formed from almost enamel only, shows a bluish hue; however, the other parts show a yellowish to reddish hue in reflection of the hue of the dentinal layer at the deep part. As such, since a tooth has different color tones at different sites, in order to obtain superior esthetic properties for tooth restoration, it is important to prepare a plurality of curable pastes for restoration having different color tones, and to select and use, from among these curable pastes for restoration, a curable paste having a color tone that is most suitable for the actual restored tooth and adjacent teeth thereof (hereinafter, also referred to as "periphery of the restored tooth") (Non-Patent Document 5).

Such selection of color tone is achieved by a dentist, who uses a shade guide (color sample) that includes a collection of various cured article samples of prepared curable pastes, compares the respective color tones of the samples with the color tone of the periphery of the restored tooth checked by looking into the oral cavity, and selecting a color tone that is felt to be closest to the color tone of the restored tooth.

Furthermore, as long as it is not the case that the damage of the restored tooth is small with a shallow cavity, it is difficult to realize the adaptation of the color tone by means of filling of a single kind of curable paste. That is, if the cavity is deep (for example, Class 4 cavity), the color tone of a tooth is visually perceived in a state in which not only the color tone of the tooth flank part (enamel portion) but also the color tone of the deep part (dentinal portion) that shows through are combined to give a rich gradation. Therefore, a deep cavity is filled by laminating the curable pastes to be filled, by varying the color tone at a certain interval of depth, and thereby this subtle color tone is reproduced. Usually, this reproduction of color tone is carried out such that a plurality of curable pastes for dentinal restoration, which reproduce the color tones of the dentinal portion, are used and laminated from the deepest part (usually, lamination is continued while each layer is cured), and a curable paste for enamel restoration is laminated at the last surface layer (for example, see Non-Patent Documents 5 and 6).

As such, since there are individual differences and site differences in the color tone of teeth, arranging curable pastes having their color tones strictly controlled in consideration of these differences, is substantially impossible because a huge number of curable pastes are needed. Particularly, in the restoration of a cavity in which the dentine is positioned at the surface of deep parts, since the color has high value and high chroma and has a yellowish to reddish hue, and there is a large variation depending on individual differences and site differences, strict control of the color tone as described above is even more difficult.

Patent Document 1: Japanese Unexamined Patent Application, Publication No. S62-86003

Patent Document 2: Japanese Unexamined Patent Application, Publication No. S63-218703

Patent Document 3: Japanese Unexamined Patent Application, Publication No. 2001-239661

Patent Document 4: Japanese Unexamined Patent Application, Publication No. 2004-276492

Patent Document 5: Japanese Unexamined Patent Application (Translation of PCT Application), Publication No. 2007-532518

Patent Document 6: PCT International Publication No. WO 2011/158742

Non-Patent Document 1: SHINODA, Hiroyuki and FUJIEDA, Ichiro, "Shikisai Kogaku Nyumon", Morikita Publishing Co., Ltd., 1$^{st}$ print published on May 1, 2007, pp. 73-78

Non-Patent Document 2: SAITO, Katsuhiro, et al., "Hikari to Shikisai no Kagaku", Kodansha, Ltd., 1$^{st}$ print published on Oct. 20, 2010, pp. 118-139

Non-Patent Document 3: The Color Science Association of Japan, ed., "Handbook of Color Science (3$^{rd}$ Edition)", University of Tokyo Press, published in April, 2011, pp. 1130-1181

Non-Patent Document 4: JIS 28102, 28110

Non-Patent Document 5: MATSUMURA, Hideo and TAGAMI, Junji, rev., "Adhesion Yearbook 2006", 1$^{st}$ Edition, Quintessence Publishing Co., Ltd., published in August, 2006, pp. 129-137

Non-Patent Document 6: MIYAZAKI, Masashi, "Science & Technique of Composite Resin Restoration", 1$^{st}$ Edition, Quintessence Publishing Co., Ltd., published in January, 2010, pp. 48-49

DISCLOSURE OF THE INVENTION

Problems to be Solved by the Invention

Restoration of teeth using a curable composition that utilizes light colored by a structural color caused by interference, diffraction, refraction, scattering or the like of light, is advantageous because a colorant substance such as a pigment may not be used. However, a curable composition that can be adapted in the restoration of teeth, by using a minimal number of color species, to the color tone of natural teeth, which have individual differences or shades of color depending on the restoration site, is desired.

Therefore, an object of the present invention is to provide a curable composition having satisfactory restoration workability for a cavity, particularly a cavity including dentine in the deep part, the curable composition forming a cured article having an appearance that matches the appearance of natural teeth and sustains the match with natural teeth for a long time period, and to provide a dental filling restorative material consisting of this composition.

Means for Solving the Problems

In view of the problems described above, the inventors of the present invention have conducted a thorough investigation. As a result, the inventors found that a curable composition which exhibits unique color tone behavior in a state of having formed a cured article, by developing a reddish hue on a black background and showing substantially white color on a white background without emitting colored light, has excellent color tone adaptability to natural teeth, and thus the problems described above can be solved. Thus, the inventors completed the present invention.

That is, the curable composition of the present invention includes a polymerizable monomer component (A); a spherical filler (B) having an average particle size in the range of 230 nm to 1,000 nm; and a polymerization initiator (C), in which when measurement is made for the curable composition in a state of having formed a cured article having a thickness of 1 mm, using a color difference meter, the cured article of the curable composition gives out a colored light having a value (V) of less than 5 and a chroma (C) of 0.05 or greater in the colorimetric values according to the Munsell Color System on a black background, and having a value (V) of 6 or greater and a chroma (C) of less than 2 in the colorimetric values according to the Munsell Color System on a white background.

The curable composition described above is obtained by selecting, as the spherical filler (B), a spherical filler having a particle size distribution in which 90% or more of constituent individual particles exist in the range of the average particle size plus or minus 5%, and
respectively selecting, as the polymerizable monomer component (A) and the spherical filler (B), a monomer component and a spherical filler that satisfy condition (X1) represented by the following Formula (1):

$$nP<nF \tag{1}$$

wherein nP represents the refractive index at 25° C. of a polymer obtainable by polymerizing the polymerizable monomer component (A); and nF represents the refractive index at 25° C. of the spherical filler (B).

In order for the curable composition to have superior color tone adaptability to natural teeth, the difference between the refractive index of the spherical filler (B), nF (25° C.), and the refractive index of a polymer of the polymerizable monomer component (A), nP (25° C.) is preferably 0.001 or more, more preferably 0.002 or more, and most preferably 0.005 or more.

According to a preferred embodiment of the present invention, a plurality of kinds of (meth)acrylic compounds are included as the polymerizable monomer component (A), and the refractive indices (25° C.) of the polymerizable monomer components (A) are in the range of 1.38 to 1.55.

According to another preferred embodiment of the present invention, the spherical filler (B) is spherical silica-titanium group oxide-based composite oxide particles, and the refractive index (25° C.) of the filler is in the range of 1.45 to 1.58.

The dental filling restorative material of the present invention consists of the curable composition described above.

In regard to the dental filling restorative material, it is preferable that the average particle size of the spherical filler (B) is in the range of 230 nm to 500 nm. This dental filling restorative material is suitable for the restoration of a cavity in which the dentine is positioned at the surface of deep parts.

The average particle size of the spherical filler (B) is more preferably in the range of 260 nm to 350 nm. This dental filling restorative material is suitable for the restoration of a cavity in which the dentine is a part having a brown-reddish color tone.

EFFECTS OF THE INVENTION

The curable composition of the present invention and a dental filling restorative material using this composition have satisfactory cavity restoration workability for the restoration of teeth, and enables restoration by which the external appearance of a cured article formed therefrom matches the appearance of natural teeth, and the match of the appearance with natural teeth is sustained for a long time period.

PREFERRED MODE FOR CARRYING OUT THE INVENTION

The curable composition of the present invention includes a polymerizable monomer (A), a spherical filler (B) having an average particle size in the range of 230 nm to 1,000 nm, and a polymerization initiator (C).

The curable composition of the present invention exhibits unique color tone behavior, in which when measurement is made for the curable composition in a state of having formed a cured article having a thickness of 1 mm, using a color difference meter, the cured article of the curable composition gives out a colored light having a value (V) of less than 5 and a chroma (C) of 0.05 or greater in the colorimetric values according to the Munsell Color System on a black background (backing having a value of 1 according to the Munsell Color System), and having a value (V) of 6 or greater and a chroma (C) of less than 2 in the colorimetric values according to the Munsell Color System on a white background (backing having a value of 9.5 according to the Munsell Color System). The value (V) of the colored light on a black background is preferably 4.5 or less, and more preferably 4.0 or less. The chroma (C) of the colored light on a black background is preferably 0.07 or greater, and more preferably 0.09 or greater. The value (V) of the colored light on a white background is preferably 6.5 or greater, and more preferably 7.0 or greater. The chroma (C) of the colored light on a white background is preferably 1.5 or less, and more preferably 1.2 or less.

Since the average particle size of the spherical filler (B) included in the composition is 230 nm to 1,000 nm, the colored light on a black background is yellowish to reddish, and specifically, the hue (H) in the colorimetric values obtained by measuring the colored light according to the Munsell Color System is in the range of 0 P or greater and less than 10 P, 0 RP or greater and less than 10 RP, 0 R or greater and less than 10 R, 0 YR or greater and less than 10 YR, 0 Y or greater and less than 10 Y, and 0 GY or greater and less than 10 GY. Preferably, the hue (H) is in the range of 0 P or greater and less than 10 P, 0 RP or greater and less than 10 RP, 0 R or greater and less than 10 R, 0 YR or greater and less than 10 YR, and 0 Y or greater and less than 10 Y; and more preferably in the range of 0 RP or greater and less than 10 RP, 0 R or greater and less than 10 R, 0 YR or greater and less than 10 YR, and 0 Y or greater and less than 10 Y.

In this way, in regard to the nature that gives a reddish hue on a black background, as long as the environment is an environment in which the periphery of the cured article exhibits a reddish color, even if the environment changes into various colors ranging from red-yellow color to red-brown color, the value, chroma, and hue all satisfactorily match. Specifically, in a case in which the chromaticity (hue and chroma) of the background (backing environment) is high, external light such as radiated light is absorbed by a background having high chromaticity, and light other than the colored light given out by the cured article is suppressed. Therefore, an observation of the colored light can be made. Meanwhile, in a case in which the chromaticity of teeth on the background (backing environment) is low, external light such as radiated light is scattered at the background of low chromaticity, and since the scattered light is stronger than the colored light given out by the cured article, the colored light is canceled and is attenuated. Therefore, in regard to the cured article of the curable composition of the present invention, a strong colored light is given out in a backing environment with high chromaticity, and a weak colored light is given out in a backing environment with low chromaticity. Therefore, an effect in which the colored light matches a wide range of reddish colors of various surrounding environments is exhibited.

A curable composition that exhibits such unique color tone behavior is obtained by using a spherical filler (B) having a particular average particle size and a narrow particle size distribution, which will be explained below, and by selecting the polymerizable monomer component (A) and the spherical filler (B) such that the relation between the refractive index of a polymer of the polymerizable monomer component (A) and the refractive index of the spherical filler (B) satisfies condition (X1) represented by the following Formula (1):

$$nP < nF \qquad (1)$$

wherein nP represents the refractive index at 25° C. of a polymer obtainable by polymerizing the polymerizable monomer component (A); and nF represents the refractive index at 25° C. of the spherical filler (B).

It is important that the average particle size of the spherical filler (B) is 230 nm to 1,000 nm, and 90% (based on number) or more of the individual particles constituting the spherical filler (B) exist within the range of the average particle size plus or minus 5%. That is, it is implied that the spherical filler (B) is composed of a large number of primary particles, and primary particles in a number equivalent to 90% or more of the total number of primary particles exist in the range of the average particle size of the large number of primary particles, plus or minus 5% (when the value of the average particle size is designated as 100%, the particle size range of the value±5%). This proportion is preferably 91% or higher, and more preferably 93% or higher. A colored light exhibiting a structural color that is expressed by interference, diffraction, refraction, scattering, or the like (hereinafter, simply referred to as "interference, scattering or the like"), is expressed when diffraction and interference occur according to Bragg conditions, and light having a particular wavelength is emphasized, or light other than a light having a particular wavelength is scattered while the light having a particular wavelength is reflected. Thus, when a spherical filler having the above-mentioned average particle size and particle size distribution is incorporated, a cured article of the curable composition exhibits a yellowish to reddish colored light according to the average particle size of the spherical filler. From the viewpoint of further enhancing the effect of expressing colored light by interference, scattering or the like, the average particle size of the spherical filler is preferably in the range of 230 nm to 800 nm, more preferably in the range of 230 nm to 500 nm, and most preferably in the range of 260 nm to 350 nm. When a spherical filler having an average particle size of less than 230 nm is used, bluish coloration occurs, and the coloration does not match the color tone of the dentine. Furthermore, when a spherical filler having an average particle size of less than 100 nm is used, a structural color is not likely to be produced. Meanwhile, when a spherical filler having an average particle size of larger than 1,000 nm is used, expression of interference, scattering or the like of light can be expected; however, since settling of the spherical filler or deterioration of abradability occurs, the curable composition is not preferable as a dental filling restorative material.

The curable composition of the present invention exhibits a yellowish to reddish colored light depending on the average particle size of 230 nm to 1,000 nm of the spherical filler (B). As explained above, in regard to the crown part, the dentine is positioned in most of the deep part of a restored cavity except for the incisal part, the dentine has high value and high chroma and has a yellowish to reddish hue (particularly reddish hue ranging from reddish yellow to reddish brown), and the variation depending on individual differences and site differences is large. Therefore, in the case of restoring such a cavity in which the surface of the deep part is positioned at the dentine, it has been hitherto especially difficult to adapt the color tone. The deep part of a restored cavity means the cavity floor of the restored cavity and the sidewall part in the lower part than the surface layer where enamel is located. In this regard, when the curable composition of the present invention in which a spherical filler (B) having the above-mentioned average particle size and particle size distribution is incorporated is used, the yellowish to reddish structural color described above is expressed, the structural color satisfactorily matches the color tone of dentine in the background, and thus a restored part having excellent adaptability to the tooth after restoration is obtained. Meanwhile, when a spherical filler having an average particle size in the range of 150 nm or more and less than 230 nm is used, the colored light thus obtained is bluish and does not match the color tone of the dentinal surface at the deep part.

As such, when the present curable composition is used, a colored light caused by interference, scattering or the like of light can be clearly recognized, and a filling restorative material that can form a restored site having an external appearance close to that of natural teeth can be obtained without using a dye substance, a pigment substance, or the like. In an area where a structural color is produced by interference of light, it is considered that the relation between the particle size of the spherical filler and the interference phenomenon of light is dependent on the Bragg diffraction conditions.

There are individual differences in the color tone of natural teeth, and the color tone may vary depending on the site to be restored; however, the curable composition of the present invention that utilizes the phenomenon of interference, scattering or the like of light can cope with various color tones. Specifically, when the chromaticity (hue and chroma) of the tooth as a background (backing) is high, external light such as radiated light is absorbed by the background having high chromaticity, and light other than the colored light (interference light, scattered and reflected light, or the like) given out from a cured article of the curable composition that utilizes the phenomenon of interference, scattering or the like of light, is suppressed. Therefore, an observation of colored light can be made. Meanwhile, when the chromaticity of the tooth as a background (backing) is low, external light such as radiated light is scattered at the background having low chromaticity, and since the scattered light is stronger than the colored light (interference light, scattered and reflected light, or the like) given out by a cured article of the curable composition that utilizes the phenomenon such as interference, scattering or the like of light, the colored light is canceled and attenuated.

As explained above, a strong colored light is given out with respect to a natural tooth having high chromaticity, and a weak colored light is given out with respect to a tooth having low chromaticity. Therefore, the curable composition of the present invention has a wide range of color tones that can be covered by a single kind of paste, and wide color tone adaptability is obtained with pastes of fewer colors than conventional pastes. As such, adapting the color tone of natural teeth with pastes of fewer colors without depending on the magnitude of chromaticity, is not easily achieved by conventional pastes that are adjusted by mixing of coloring substances such as pigments.

The curable composition of the present invention has a feature that a colored light is produced by the phenomenon of interference, scattering, or the like; and whether the colored light will be given out can be checked by measuring the spectral reflectance characteristics using a color difference meter under the conditions of both on a black background and on a white background. On a black background, when the above-mentioned conditions are satisfied, a characteristic reflection visible spectrum corresponding to the colored light is clearly recognized; however, on a white background, the curable composition shows a substantially uniform reflectance substantially over the whole range of visible light (380 to 780 nm). Thus, a particular reflection visible spectrum is not recognized, and the curable composition is substantially colorless. This is speculated to be because external light (for example, C light source or D65 light source) is absorbed or blocked on a black background, and a colored light caused by interference, scattering or the like is emphasized; whereas on a white background, since scattered light of external light is strong, a colored light caused by interference, scattering or the like is not easily observed.

In order to obtain the effects of the present invention, it is important that the relation between the refractive index nP of a polymer of the polymerizable monomer component and the refractive index nF of the spherical filler satisfy condition (X1) represented by Formula (1):

$$nP<nF \qquad (1).$$

As shown by Formula (1), in regard to the curable composition of the present invention, the relation between the refractive indices of a polymer of the polymerizable monomer component and the spherical filler is such that $nP<nF$. When the refractive index of the spherical filler is high, and the refractive index of the polymer as a matrix is low, a colored light caused by interference, scattering or the like is strongly expressed; however, in an opposite case, light having short wavelengths are more easily subjected to interference or scattering, the colored light thus obtainable has shorter wavelengths and have bluish tint, and the color tone adaptability to restoration sites of various color tones is likely to become poor.

Hereinafter, the various components of the curable composition of the present invention will be explained.

<Polymerizable Monomer Component (A)>

Regarding the polymerizable monomer component, any known monomer can be used without particular limitations. In the aspect of dental applications, from the viewpoint of the polymerization rate, a radical polymerizable or cationic polymerizable monomer is preferred. Particularly preferred examples of the radical polymerizable monomer include a (meth)acrylic compound. Examples of the (meth)acrylic compound include (meth)acrylates given below. Particularly preferred examples of the cationic polymerizable monomer include epoxies and oxetanes.

Generally, examples of the (meth)acrylates that are suitably used include the compounds listed under the following items (I) to (III).

(I) Bifunctional Polymerizable Monomers
(i) Aromatic Compound-Based Monomers
2,2-Bis(methacryloyloxyphenyl)propane,
2,2-bis[(3-methacryloyloxy-2-hydroxypropyloxy)phenyl]propane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane,
2(4-methacryloyloxydiethoxyphenyl)-2(4-methacryloyloxytriethoxyphenyl)propane, 2(4-methacryloyloxydipropoxyphenyl)-2-(4-methacryloy-loxytriethoxyphenyl)propane,
2,2-bis(4-methacryloyloxypropoxyphenyl)propane,
2,2-bis(4-methacryloyloxyisopropoxyphenyl)propane,
and acrylates corresponding to these methacrylates;
diadducts obtainable from addition of vinyl monomers having an —OH group, such as methacrylates such as 2-hydroxyethyl methacrylate,
2-hydroxypropyl methacrylate, and
3-chloro-2-hydroxypropyl methacrylate, or acrylates corresponding to these methacrylates, and diisocyanate compounds having an aromatic group, such as diisocyanatomethylbenzene and 4,4'-diphenylmethane diisocyanate.

(ii) Aliphatic Compound-Based Monomers
Ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-hexanediol dimethacrylate,
and acrylates corresponding to these methacrylates;
diadducts obtainable from adducts between vinyl monomers having an —OH group, such as methacrylates such as 2-hydroxyethyl methacrylate,
2-hydroxypropyl methacrylate,
3-chloro-2-hydroxypropyl methacrylate, or acrylates corresponding to these methacrylates, and
diisocyanate compounds such as hexamethylene diisocyanate, trimethylhexamethylene diisocyanate, and
diisocyanatomethylcyclohexane, isophorone diisocyanate, and methylenebis(4-cyclohexyl isocyanate), for example,
1,6-bis(methacrylethyloxycarbonylamino)trimethylhexane;
1,2-bis(3-methacryloyloxy-2-hydroxypropoxy)ethyl, and the like.

(II) Trifunctional Polymerizable Monomers
Methacrylates such as trimethylolpropane trimethacrylate,
trimethylolethane trimethacrylate
pentaerythritol trimethacrylate, and
trimethylolmethane trimethacrylate, acrylates corresponding to these methacrylates, and the like.

(III) Tetrafunctional polymerizable Monomers
Pentaerythritol tetramethacrylate,
pentaerythritol tetraacrylate; and
diadducts obtainable from adducts between diisocyanate compounds such as diisocyanatomethylbenzene,
diisocyanatomethylcyclohexane,
isophorone diisocyanate,
hexamethylene diisocyanate,
trimethylhexamethylene diisocyanate,
methylenebis(4-cyclohexyl isocyanate),
4,4-diphenylmethane diisocyanate, and
tolylene-2,4-diisocyanate, and glycidol dimethacrylate, and the like.

Regarding these polyfunctional (meth)acrylate-based polymerizable monomers, a plurality of kinds of compounds may be used in combination as necessary.

Furthermore, if necessary, monofunctional (meth)acrylate-based monomers, such as methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates; and polymerizable monomers other than the above-mentioned (meth)acrylate-based monomers may also be used.

According to the present invention, as the polymerizable monomer component (A), generally, a plurality of polymerizable monomers are used for the purpose of regulating the physical properties of the cured article (mechanical characteristics and adhesiveness to dentine). At this time, it is desirable that the types and the mixing ratio of the polymerizable monomers are set such that the refractive index of the component (A) is in the range of 1.38 to 1.55. That is, by setting the refractive index of the component (A) to be in the range of 1.38 to 1.55, the refractive index nP of the polymer obtainable from the polymerizable monomer component (A) can be set to be approximately in the range of 1.40 to 1.57. There are cases of using a plurality of kinds of polymerizable monomers; however, regarding the refractive index in this case, it is acceptable as long as the refractive index of the mixture of a plurality of polymerizable monomers is in the above-mentioned range, and the refractive indices of the individual polymerizable monomers may not be always in the range described above.

The refractive indices of polymerizable monomers and polymers thereof can be determined at 25° C. using an Abbe refractometer.

<Spherical Filler (B)>
A general curable composition includes various filler materials such as inorganic powders and organic powders; however, the curable composition of the present invention includes a spherical filler (B) having an average particle size of 230 nm to 1,000 nm, for the purpose of expressing a colored light caused by interference, scattering, or the like. A feature of the curable composition of the present invention is that the constituent filler material is spherical in shape and has a narrow particle size distribution. A colored light caused by interference is produced at an area where constituent particles are relatively regularly accumulated, and a colored light caused by scattering is produced at an area where constituent particles are disorderly dispersed. The spherical filler (B) that constitutes the curable composition of the present invention is spherical in shape and has a narrow particle size distribution, and therefore, a colored light caused by interference, scattering or the like is produced. Meanwhile, when irregularly shaped particles that are produced by pulverization or the like are used, the particle size distribution is wide, and the shape is also non-uniform. Therefore, the particles are not regularly accumulated, and a colored light is not produced.

The phrase "spherical filler is relatively regularly accumulated" as used in the present invention means a state in which the spherical filler is uniformly dispersed in the polymerizable monomer component, and the particles are arranged in an isotropic structure with certain orderliness.

Regarding the spherical filler (B), any filler that is used as a component of a general curable composition in the field of dentistry can be used without limitations as long as the requirements for the average particle size and the particle size distribution as described below are satisfied; however, specific examples include inorganic powders such as amorphous silica, silica-titanium group oxide-based composite oxide particles (silica-zirconia, silica-titania, and the like), quartz, alumina, barium glass, zirconia, titania, lanthanoids, and colloidal silica. Furthermore, organic powders or organic-inorganic composite powders can also be used.

Among these, silica-titanium group oxide-based composite oxide particles are preferred from the viewpoint that the refractive index is easily adjustable.

As described above, the average particle size of the spherical filler (B) is 230 nm to 1,000 nm, and depending on the particle size, a cured article of the curable composition exhibits a yellowish to reddish colored light. However, among these, when a spherical filler having an average particle size in the range of 230 nm to 260 nm is used, the colored light thus obtainable is yellowish, and the curable composition is useful for the restoration of a cavity in which the color tone of the tooth flank in the periphery of the restored tooth is in the class of B system (red-yellow) according to Shade Guide "VITAPAN Classical (registered trademark)". When a spherical filler having an average particle size in the range of 260 nm to 350 nm is sued, the colored light thus obtainable is reddish, and the curable composition is useful for the restoration of a cavity in which the color tone of the tooth flank in the periphery of the restored tooth is in the class of A system (red-brown) according to Shade Guide "VITAPAN Classical (registered trademark)". Since the hue of the dentine is reddish as such in many cases, in the present invention, an embodiment of using a spherical filler having an average particle size in the range of 260 nm to 350 nm as such, is most preferred because adaptability to restored teeth having a variety of color tones is improved to a large extent.

It is important for the spherical filler that the primary particle size is in the range of the average value described above, and as long as this requirement is satisfied, the individual primary particles may exist as more or less aggregate particles. However, it is preferable that the primary particles exist as independent particles as far as possible, and specifically, it is preferable that the proportion of aggregate particles having a size of 10 μm or more is less than 10% by volume.

According to the present invention, the average particle size of the spherical filler (B) is obtained by taking photographs of the powder by scanning electron microscopy, measuring the number of whole particles (30 particles or more) and the primary particle size (maximum diameter) of the whole particles observed within a unit viewing field of the photograph, and calculating average values by the following formula based on the measurement values thus obtained.

$$\overline{x} = \frac{\sum_{i=1}^{n} x_i}{n} \text{ (Number average)}$$

(n: number of particles, $x_i$: primary particle size (maximum diameter) of i-th particle)

According to the present invention, regarding the proportion (%) of particles in the range of the average particle size ±5% of the spherical filler (B), the number of particles having a primary particle size (maximum diameter) that was not in the particle size range of the average particle size ±5% determined as described above, among the whole particles (30 particles or more) within a unit viewing field of the above-mentioned photograph, was measured, the value was subtracted from the number of whole particles, the number of particles in the particle size range of average particle size ±5% within a unit viewing field of the photograph was determined, and the proportion of particles in the range of the average particle size ±5% was calculated by the following formula:

Proportion (%) of particles in the range of average particle size ±5% of spherical filler (B)=[(number of particles in the particle size range of average particle size ±5% within a unit viewing field of scanning electron microscopic photograph)/(number of whole particles within a unit viewing field of scanning electron microscopic photograph)]×100.

Here, the spherical shape of the spherical filler may be an approximate spherical shape, and the shape is not necessarily essential to be a perfect true sphere. Generally, when a photograph of particles by scanning electron microscope is taken, and the average uniformity ratio is calculated by dividing the particle size in a direction perpendicular to the maximum diameter for each of the particles (30 particles or more) within a unit viewing field of the photograph, by the maximum diameter, the average uniformity ratio may be 0.6 or greater, and more preferably 0.8 or greater.

The silica-titanium group oxide-based composite oxide particles according to the present invention are composite oxide of silica and a titanium group (elements of Group IV in the Periodic Table of Elements) oxide, and examples include silica-titania, silica-zirconia, and silica-titania-zirconia. Among these, silica-zirconia is preferred since the refractive index of the filler is adjustable, and high X-ray opacity can also be imparted. The composite ratio is not particularly limited; however, from the viewpoint of imparting sufficient X-ray opacity and thereby adjusting the refractive index to a suitable range that will be described below, it is preferable that the content of silica is 70 mol % to 95 mol %, and the content of the titanium group oxide is 5 mol % to 30 mol %. In the case of silica-zirconia, the refractive index can be freely varied by varying the respective composite ratio as such.

Meanwhile, in these silica-titanium group oxide-based composite oxide particles, incorporation of metal oxides other than silica and titanium group oxides is also allowed, as long as the amount is small. Specifically, an alkali metal oxide such as sodium oxide or lithium oxide may be incorporated within an amount of 10 mol %.

A method for producing such silica-titanium group oxide-based composite oxide particles is not particularly limited; however, in order to obtain the particular spherical filler of the present invention, for example, a so-called sol-gel method of adding a mixed solution including a hydrolyzable organosilicon compound and a hydrolyzable organotitanium group metal compound to an alkaline solvent, performing hydrolysis, and precipitating a reaction product, is suitably employed.

These silica-titanium group oxide-based composite oxide particles may be surface-treated with a silane coupling agent. As a result of surface treatment using a silane coupling agent, particles having excellent interfacial strength between the silica-titanium group oxide-based composite oxide particles and the polymer portion of the polymerizable monomer component (A) is obtained. Representative examples of the silane coupling agent include organosilicon compounds such as γ-methacryloyloxyalkyltrimethoxysilane and hexamethyldisilazane. The amount of surface treatment with these silane coupling agents is not particularly limited, and an optimal value may be determined after the mechanical properties and the like of a curable composition thus obtainable are checked in advance by experiments. However, an example of a suitable range is the range of 0.1 to 15 parts by weight with respect to 100 parts by weight of the particles.

As explained above, a colored light caused by interference, scattering or the like, which exhibits satisfactory color tone adaptability to natural teeth, is obtained in a case in which the relation of the following Formula (1) is satisfied:

$$nP < nF \qquad (1)$$

wherein nP represents the refractive index at 25° C. of a polymer obtainable by polymerizing the polymerizable monomer component (A); and nF represents the refractive index at 25° C. of the spherical filler (B).

That is, the refractive index of the spherical filler (B) is in a state of being higher than the refractive index of a polymer obtainable by polymerizing the polymerizable monomer component (A). The difference between the refractive index nF (25° C.) of the spherical filler (B) and the refractive index nP (25° C.) of a polymer of the polymerizable monomer component (A) is preferably 0.001 or more, more preferably 0.002 or more, and most preferably 0.005 or more. In regard to the refractive index, since the refractive index is clearly expressed in a case in which the cured article has high transparency, regarding the spherical filler (B), it is preferable to select and use a spherical filler whose difference in the refractive index with a polymer of the polymerizable monomer component (A) is 0.1 or less, and more preferably 0.05 or less, and which does not impair transparency as far as possible.

The amount of incorporation of the spherical filler (B) according to the present invention is 50 to 1,500 parts by mass with respect to 100 parts by mass of the polymerizable monomer component (A). When silica-titanium group oxide-based composite oxide particles are incorporated in an amount of 50 parts by mass or more, a colored light caused by interference, scattering or the like is satisfactorily expressed. Furthermore, in the case of using composite oxide particles whose difference in the refractive index with a polymer of the polymerizable monomer component (A) is more than 0.1, there is a risk that transparency of the cured article may be deteriorated, and the effect of expressing a colored light is also not sufficiently exhibited. In consideration of these, the amount of incorporation of the spherical filler (B) is suitably 100 to 1,500 parts by mass, and particularly suitably 150 to 1,500 parts by mass, with respect to 100 parts by mass of the polymerizable monomer component (A).

In the spherical filler (B), the refractive index of the silica-based filler, particularly the silica-titanium group oxide-based composite oxide, is in the range of about 1.45 to 1.58 depending on the content of silica component. That is, by setting the refractive index of the polymerizable monomer component (A) to the above-described range (range of 1.38 to 1.55), the spherical filler (B) can be easily selected so as to satisfy the above-mentioned condition (X1). That is, it is desirable to use a silica-titanium group oxide-based composite oxide (for example, silica-titania or silica-zirconia) containing an appropriate amount of silica component.

<Polymerization Initiator (C)>

The polymerization initiator used in the present invention is incorporated for the purpose of polymerizing and curing the present composition; however, any known polymerization initiator can be used without particular limitations.

Above all, in the direct filling restoration applications in dentistry, where curing is frequently performed within the oral cavity, a photopolymerization initiator or a chemical polymerization initiator composition is preferred, and from the viewpoint of being convenient without the need for mixing operation, a photopolymerization initiator (composition) is preferred.

Examples of the polymerization initiator that is used for photopolymerization include benzoin alkyl ethers such as benzoin methyl ether, benzoin ethyl ether, and benzoin isopropyl ether; benzyl ketals such as benzyl dimethyl ketal and benzyl diethyl ketal; benzophenones such as benzophenone, 4,4'-dimethylbenzophenone, and 4-methacryloxybenzophenone; α-diketones such as diacetyl, benzyl 2,3-pentadione, camphor-quinone, 9,10-phenanthraquinone, and 9,10-anthraquinone; thioxanthone compounds such as 2,4-diethoxythioxanthone, 2-chlorothioxanthone, and methylthioxanthone; and bisacylphosphine oxides such as bis-(2,6-dichlorobenzoyl)phenylphosphine oxide, bis(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis (2,4,6-trimethylbenzoyl)-phenylphosphine oxide.

Regarding the photopolymerization initiator, a reducing agent is frequently added. Examples of such a reducing agent include tertiary amines such as 2-(dimethylamino) ethyl methacrylate, ethyl 4-dimethylaminobenzoate (ethyl p-N,N-dimethylaminobenzoate), and N-methyldiethanolamine; aldehydes such as lauryl aldehyde, dimethylaminobenzaldehyde, and terephthalic aldehyde; and sulfur-containing compounds such as 2-mercaptobenzoxazole, 1-decanethiol, thiosalicylic acid, and thiobenzoic acid.

Furthermore, cases of using a composition by adding a photoacid generator, in addition to the photopolymerization initiator and the reducing compound, may be frequently seen. Examples of such a photoacid generator include a diaryliodonium salt-based compound, a sulfonium salt-based compound, a sulfonic acid ester compound a halomethyl-substituted-S-triazine derivative, and a pyridinium salt-based compound.

According to the present invention, since the change in color tone of the curable composition caused by the silica-titanium group oxide-based composite oxide particles occurs noticeably when an amine compound is incorporated as a reducing agent into the polymerization initiator, it is particularly effective in the present invention that such an amine compound is used in combination with a polymerization initiator.

These polymerization initiators may be used singly, or two or more kinds thereof may be used as mixtures. Regarding the amount of incorporation of the polymerization initiator, an effective amount may be selected according to the purpose; however, the polymerization initiator is usually used at a proportion of 0.01 to 10 parts by weight, and more preferably at a proportion of 0.1 to 5 parts by weight, with respect to 100 parts by weight of the polymerizable monomer.

<Other additives>

In the curable composition of the present invention, other known additives can be incorporated, in addition to the components (A) to (C), to the extent that the effect of the curable composition is not impaired. Specific examples include a polymerization inhibitor and an ultraviolet absorber. Furthermore, for the purpose of viscosity adjustment or the like, a filler having a particle size that is sufficiently smaller than the wavelength of light and does not easily affect the color tone or transparency, can be incorporated.

In the present invention, as described above, even if a coloring substance such as a pigment is not used, the range of color tone that can be covered by a single kind of paste (curable composition) is wide, broad color tone adaptability to natural teeth is obtained with pastes of fewer color types, and satisfactory restoration is enabled. Therefore, an embodiment in which a pigment, for which there is a risk of discoloration occurring with the lapse of time, is not incorporated is preferred. However, according to the present invention, it is not meant to deny the incorporation of a pigment itself, and a pigment may be incorporated to the extent that will not interfere with a colored light caused by interference, scattering or the like of the spherical filler. Specifically, a pigment in an amount of about 0.0005 to 0.5 parts by mass, and preferably about 0.001 to 0.3 parts by mass, with respect to 100 parts by mass of the polymerizable monomer may be incorporated.

The curable composition of the present invention is particularly suitably used as a dental filling restorative material represented by a photocurable composite resin such as described above; however, the curable composition is not limited to that use and can also be suitably used for other applications. Examples of such an application include dental cement, and a restorative material for abutment construction.

EXAMPLES

Hereinafter, the present invention will be more specifically described by way of Examples; however, the present invention is not limited to these Examples.

The methods for measuring various physical properties according to the present invention are as follows.

(1) Average Particle Size of Spherical Filler

Photographs of a powder were taken by a scanning electron microscope (manufactured by Philips N.V., "XL-30S"), and the number of whole particles (30 particles or more) observed within a unit viewing field of the photographs and the primary particle size (maximum diameter) of the whole particles were respectively measured. Based on the measured values thus obtained, the average particle size was calculated by the following formula.

$$\bar{x} = \frac{\sum_{i=1}^{n} x_i}{n} \quad \text{(Number average)}$$

(n: number of particles, $x_i$: primary particle size (maximum diameter) of i-th particle)

(2) Proportion of Particles in Range of Average Particle Size±5%

Among the whole particles (30 particles or more) within a unit viewing field of the photographs taken in (1), the number of particles having a primary particle size (maximum diameter) in the particle size range of average particle size ±5% as determined in (1) was measured, the value was subtracted from the number of the whole particles, and the number of particles in the particle size range of average particle size ±5% within a unit viewing field of the photographs was determined. Thus, the proportion was calculated by the following formula:

Proportion (%) of particles in range of average particle size ±5% of spherical filler (B)=[(Number of particles in particle size range of average particle size ±5% in unit viewing field of scanning electron microscopic photograph)/(number of whole particles in unit viewing field of scanning electron microscopic photograph)]×100.

(3) Measurement of Refractive Index

<Refractive Index of Polymerizable Monomer Component (A)>

The refractive indices of the polymerizable monomer and a mixture thereof were measured in a constant temperature chamber at 25° C. using an Abbe refractometer (manufactured by Atago Co., Ltd.).

<Refractive Index nP of Polymer>

The refractive index of a polymer of a polymerizable monomer (or a mixture of polymerizable monomers) was measured in a constant temperature chamber at 25° C. using a polymer polymerized under conditions that were almost the same as the polymerization conditions in a cavity, and using an Abbe refractometer (manufactured by Atago Co., Ltd.).

That is, a uniform polymerizable monomer (or a mixture of polymerizable monomers) obtained by mixing 0.2% by mass of camphor-quinone (CQ), 0.3% by mass of ethyl p-N,N-dimethylaminobenzoate (DMBE), and 0.15% by mass of hydroquinone monomethyl ether (HQME) was introduced into a mold having a hole with a size of φ 7 mm×0.5 mm, and a polyester film was pressure bonded on both surfaces. Subsequently, the polymerizable monomer was cured by irradiating the polymerizable monomer with light for 30 seconds using a halogen type light irradiation apparatus for dental use (DEMETRON LC, manufactured by Sybron Dental Specialties, Inc.) at a dose of 500 mW/cm$^2$, and then the cured article was taken out from the mold. Thus, a polymer of the polymerizable monomer was produced. When the polymer was mounted in the Abbe refractometer (manufactured by Atago Co., Ltd.), for the purpose of adhering the polymer to the measurement surface, the sample was not dissolved, and a solvent having a refractive index higher than that of the sample (bromonaphthalene) was added dropwise to the sample, and measurement was made.

<Refractive Indices of Spherical Filler and Other Inorganic Filler Materials>

The refractive index nF of the spherical filler and the refractive indices of other inorganic filler material used in the Examples were measured according to a liquid immersion method using an Abbe refractometer (manufactured by Atago Co., Ltd.).

That is, in a constant temperature chamber at 25° C., 1 g of a surface-treated product of the spherical filler or the other inorganic filler material, or a surface-treated product of any one of these was dispersed in 50 ml of anhydrous toluene in a 100-ml sample bottle. While this dispersion liquid was stirred, 1-bromotoluene was slightly added dropwise thereto, and the refractive index of the dispersion liquid at the time point where the dispersion liquid became most transparent was measured. Thereby, the refractive index nF of the spherical filler and the refractive indices of the other inorganic filler materials were obtained.

(4) Evaluation of Colored Light by Visual Inspection

A paste of each of the curable compositions produced in Examples and Comparative Examples was introduced into a mold having a hole having a size of 7 mmφ×1 mm, and the two surfaces were pressure bonded with a polyester film. The paste was cured by irradiating the two surfaces with light for 30 seconds each with a visible light irradiation apparatus (manufactured by Tokuyama Corporation, POWER LIGHT), and then the cured article was taken out from the mold. A black tape (carbon tape) which measured 10 mm on each side was placed on a pressure-sensitive adhesive surface, and the color tone of the colored light was checked by visual inspection.

(5) Wavelength of Colored Light

A paste of each of the curable compositions produced in Examples and Comparative Examples was poured into a mold having a hole having a size of 7 mmφ×1 mm, and a polyester film was pressure-bonded to the two surfaces. The paste was cured by irradiating the two surfaces for 30 seconds each with a visible light irradiation apparatus (manufactured by Tokuyama Corporation, POWER LIGHT), and then the cured article was taken out from the mold. The spectral reflectance was measured on a black background (backing having a value of 1 according to the Munsell Color System) and on a white background (backing having a value of 9.5 according to Munsell Color System) using a color difference meter (manufactured by Tokyo Denshoku Co., Ltd., "TC-1800 MKII"), and the maximum point of the reflectance on the black background was designated as the wavelength of the colored light.

(6) Hue, Value, and Chroma

Cured articles having a thickness of 1 mm were produced using the respective pastes in the same manner as described above, and the hue (H), value (V), and chroma (C) based on the Munsell Color System were measured according to JIS 28722 for each of the cured articles on a black background (backing having a value of 1 according to the Munsell Color System) and on a white background (backing having a value of 9.5 according to the Munsell Color System), using a color difference meter (manufactured by Tokyo Denshoku Co., Ltd., "TC-1800 MKII").

(7) Evaluation of Color Tone Adaptability

For the evaluation of color tone adaptability, a model tooth for restoration (hard resin tooth) formed from a dentine part and an enamel part, the dentine part being covered with the enamel part, was used. A model tooth for tooth restoration (transverse diameter 9 mm, crown length 12 mm) that reproduced an incisal part loss cavity (width 2 mm, height 1 mm) of the upper right #1, a model tooth for tooth restoration (transverse diameter 10 mm) that reproduced a Class I cavity (diameter 4 mm, depth 2 mm) of the lower right #6, or a model tooth for tooth restoration (transverse diameter 9 mm, crown length 12 mm) that reproduced a tooth cervix loss cavity (diameter 4 mm, depth 2 mm) of upper right #3 was used. The cavity was filled with a curable paste, the paste was polished after curing, and the color tone adaptability was checked by visual inspection. Furthermore, for the model teeth for tooth restoration, a high chromaticity model tooth of high chroma and a low chromaticity model tooth of low chroma in the class of A system (red-brown) according to Shade Guide "VITAPAN Classical (registered trademark)" was used, and a high chromaticity model tooth of high chroma and a low chromaticity model tooth of low chroma in the class of B system (red-yellow) according to Shade Guide "VITAPAN Classical (registered trademark)" was used.

Evaluation criteria for color tone adaptability:

A: The color tone of the restored material satisfactorily matches the color tone of the model tooth for tooth restoration.

According to the high degree of adaptability, the color tone adaptability was evaluated in more detail in two stages of A1>A2.

B: The color tone of the restored material is similar to the color tone of the model tooth for tooth restoration.

According to the degree of similarity, the color tone was evaluated in more detail in two stages of B1>B2.

C: The color tone of the restored material is similar to the color tone of the model tooth for tooth restoration; however, adaptability is not satisfactory.

D: The color tone of the restored material is not compatible with the color tone of the model tooth for tooth restoration.

(8) Change in Color Tone Over Time

A paste of each of the curable compositions produced in Examples and Comparative Examples was introduced into a mold having a hole having a size of 7 mmϕ×1 mm, and a polyester film was pressure-bonded to the two surfaces. The paste was cured by irradiating the two surfaces with light for 30 seconds each using a visible light irradiation apparatus (manufactured by Tokuyama Corporation, POWER LIGHT), and then the cured article was taken out from the mold. The cured article was stored for 4 months at 37° C. in water, the color tone was measured using a color difference meter (manufactured by Tokyo Denshoku Co., Ltd.; TC-1800 MKII), and the difference between the color tones measured before and after storage was designated as $\Delta E^*$.

$$\Delta E^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

wherein $L1^*$: value index of the cured article after storage, $a1^*$, $b1^*$: color quality index of the cured article after storage, $L2^*$: value index of the cured article before storage, $a2^*$, $b2^*$: color quality index of the cured article before storage, and $\Delta E^*$: amount of color tone change.

The polymerizable monomers, polymerization initiator, and the like used in the Examples and Comparative Examples are as follows.

[Polymerizable Monomers]
  1,6-Bis(methacrylethyloxycarbonylamino)trimethylhexane (hereinafter, abbreviated to "UDMA")
  Triethylene glycol dimethacrylate (hereinafter, abbreviated to "3G")
  2,2-Bis[(3-methacryloyloxy-2-hydroxypropyloxy)phenyl]propane (hereinafter, abbreviated to "bis-GMA")

[Polymerization Initiator]
  Camphor-quinone (hereinafter, abbreviated to "CQ")
  Ethyl p-N,N-dimethylaminobenzoate (hereinafter, abbreviated to "DMBE")

[Polymerization Inhibitor]
  Hydroquinone monomethyl ether (hereinafter, abbreviated to "HQME")

[Colorant]
  Titanium dioxide (white pigment)
  Pigment Yellow (yellow pigment)
  Pigment Red (red pigment)
  Pigment Blue (blue pigment)

The polymerizable monomers indicated in Table 1 were mixed, and matrices M1 and M2 were produced.

TABLE 1

| Monomer name | Polymerizable monomer component[1] | Refractive index Before curing | Refractive index After curing |
|---|---|---|---|
| M1 | UDMA(60)/3G(40) | 1.474 | 1.509 |
| M2 | bis-GMA(50)/3G(50) | 1.506 | 1.540 |
| M3 | bis-GMA(70)/3G(30) | 1.488 | 1.528 |

[1]Values within parentheses represent mixing proportions (parts by mass).

[Spherical Filler]

The production of the spherical filler was carried out using a so-called sol-gel method, by which a mixed solution including a hydrolysable organosilicon compound (tetraethyl silicate) and a hydrolysable organotitanium group metal compound (tetrabutyl zirconate or tetrabutyl titanate) was added to an ammoniacal alcohol (for example, methanol, ethanol, isopropyl alcohol, or isobutyl alcohol) solution containing aqueous ammonia incorporated therein, hydrolysis was performed, and a reaction product was precipitated, by the methods described in JP-S58-110414 A, JP-S58-156524 A, and the like.

[Irregular-Shaped Inorganic Filler]

An irregular-shaped inorganic filler was produced, by the methods described in JP-H2-132102 A, JP-H3-197311 A, and the like, by dissolving an alkoxysilane compound in an organic solvent, partially hydrolyzing the compound by adding water, subsequently adding an alkoxide of another metal for compositization and an alkali metal compound, performing hydrolysis, drying a gel-like material thus produced, subsequently pulverizing the dried product as necessary, and then calcining the dried product.

The spherical fillers and irregular-shaped inorganic fillers used in the Examples and Comparative Examples are indicated in Table 2.

TABLE 2

| Filler name | Composition and shape of filler | | Average particle size nm | Refractive index | Proportion of particles within range of average particle size ±5% % |
|---|---|---|---|---|---|
| | Composition | Shape | | | |
| PF1 | $SiO_2/ZrO_2/Na_2O$ | Spherical | 178 | 1.515 | 91 |
| PF2 | $SiO_2/ZrO_2/Na_2O$ | Spherical | 230 | 1.515 | 92 |
| PF3 | $SiO_2/ZrO_2/Na_2O$ | Spherical | 281 | 1.515 | 90 |
| PF4 | $SiO_2/ZrO_2/Na_2O$ | Spherical | 80 | 1.515 | 92 |
| PF5 | $SiO_2/ZrO_2/Na_2O$ | Spherical | 280 | 1.515 | 87 |
| PF6 | $SiO_2/ZrO_2/Na_2O$ | Spherical | 282 | 1.522 | 93 |
| PF7 | $SiO_2/ZrO_2/Na_2O$ | Spherical | 286 | 1.542 | 91 |
| PF8 | $SiO_2/TiO_2/Na_2O$ | Spherical | 280 | 1.522 | 95 |
| PF9 | $SiO_2/ZrO_2/Na_2O$ | Spherical | 340 | 1.515 | 91 |
| PF10 | $SiO_2/ZrO_2/Na_2O$ | Spherical | 260 | 1.522 | 93 |
| PF11 | $SiO_2/ZrO_2/Na_2O$ | Irregular-shaped | 500 | 1.515 | 50 |

Examples 1 to 9

0.3% by weight of CQ, 1.0% by weight of DMBE, and 0.15% by weight of HQME were added to matrix M1 or matrix M2, the mixture was mixed, and thus a uniform polymerizable monomer composition was produced. Next, the respective spherical filler indicated in Table 3 was weighed into a mortar, the matrix was gradually added thereto under red light, and the mixture was sufficiently kneaded in a dark place. Thus, a uniform curable paste was obtained. Furthermore, this paste was defoamed under reduced pressure to remove air bubbles, and thus a curable composition was produced. For the curable compositions (filling restorative materials) thus obtained, various physical properties were evaluated based on the above-described methods. The compositions and results are presented in Tables 3 and 4.

Comparative Examples 1 to 3 and 5 to 8

0.3% by weight of CQ, 1.0% by weight of DMBE, and 0.15% by weight of HQME were added to matrix M1, M2, or M3, the mixture was mixed, and a uniform polymerizable monomer composition was produced. Next, the various fillers indicated in Table 3 were weighed into a mortar, the matrix was gradually added thereto under red light, and the mixture was sufficiently kneaded in a dark place. Thus, a uniform curable paste was obtained. Furthermore, this paste was defoamed under reduced pressure to remove air bubbles, and thus a curable composition was produced. For the curable compositions (filling restorative materials) thus obtained, various physical properties were evaluated based on the above-described methods. The compositions and results are presented in Tables 3 and 4.

Comparative Example 4

0.3% by weight of CQ, 1.0% by weight of DMBE, and 0.15% by weight of HQME were added to matrix M2, the mixture was mixed, and a uniform polymerizable monomer composition was produced. Next, the spherical filler indicated in Table 3 was weighed into a mortar, and the matrix was gradually added thereto under red light. 0.050 g of titanium dioxide (white pigment), 0.001 g of Pigment Yellow (yellow pigment), 0.0005 g of Pigment Red (red pigment), and 0.0002 g of Pigment Blue (blue pigment) were further added to the mixture, and the mixture as sufficiently kneaded in a dark place. Thus, a uniform paste was obtained. Furthermore, this paste was defoamed under reduced pressure to remove air bubbles, and the a curable composition as produced. According to an evaluation by visual inspection, the color tone was a color tone that matched the A-system of high-chromaticity model tooth. Subsequently, various physical properties were evaluated based on the methods described above. The composition and results are presented in Tables 3 and 4.

TABLE 3

| Example No. | Monomer[1] | Filler[1] | Filler filling ratio | Refractive index difference[2] | Evaluation by visual inspection of colored light |
|---|---|---|---|---|---|
| Example 1 | M1 (100) | PF2 (150) | 60% | 0.006 | Yellow |
| Example 2 | M1 (100) | PF3 (150) | 60% | 0.006 | Red |
| Example 3 | M1 (100) | PF6 (150) | 60% | 0.013 | Red |
| Example 4 | M1 (100) | PF6 (150) | 60% | 0.013 | Red |
| Example 5 | M2 (100) | PF7 (150) | 60% | 0.002 | Red |
| Example 6 | M1 (100) | PF8 (150) | 60% | 0.013 | Red |
| Example 7 | M1 (100) | PF9 (150) | 60% | 0.006 | Red |
| Example 8 | M1 (100) | PF7 (150) | 60% | 0.033 | Red |
| Example 9 | M1 (100) | PF10 (150) | 60% | 0.013 | Red |
| Comparative Example 1 | M1 (100) | PF4 (150) | 60% | 0.006 | None |
| Comparative Example 2 | M1 (100) | PF5 (150) | 60% | 0.006 | Pale red |
| Comparative Example 3 | M1 (100) | PF11 (150) | 60% | 0.006 | None |
| Comparative Example 4 | M2 (100) | PF2 (150) | 60% | −0.025 | — |

TABLE 3-continued

| Example No. | | | | | |
|---|---|---|---|---|---|
| Comparative Example 5 | M2 (100) | PF3 (150) | 60% | −0.025 | Blue |
| Comparative Example 6 | M3 (100) | PF3 (150) | 60% | −0.013 | Blue |
| Comparative Example 7 | M1 (100) | PF1 (150) | 60% | 0.006 | Blue |
| Comparative Example 8 | M1 (100) | PF1 (150) | 60% | 0.006 | Blue |

| Example No. | Colored light on black background Wavelength (nm) | Colored light on white background Wavelength (nm) | Color tone on black background Hue (H) | Value (V) | Chroma (C) | Color tone on white background Hue (H) | Value (V) | Chroma (C) | Change over time in color tone ΔE* |
|---|---|---|---|---|---|---|---|---|---|
| Example 1 | 603 | No Maximum | 5.32Y | 3.10 | 0.50 | 2.15Y | 7.52 | 1.05 | 2.0 |
| Example 2 | 750 | No Maximum | 9.97YR | 3.16 | 0.07 | 1.79Y | 7.31 | 0.86 | 1.3 |
| Example 3 | 758 | No Maximum | 6.41YR | 3.54 | 0.21 | 1.30Y | 7.26 | 0.97 | 1.4 |
| Example 4 | 758 | No Maximum | 6.41YR | 3.54 | 0.21 | 1.30Y | 7.26 | 0.97 | 1.4 |
| Example 5 | 746 | No Maximum | 9.76YR | 3.32 | 0.24 | 1.83Y | 7.46 | 1.13 | 1.6 |
| Example 6 | 754 | No Maximum | 0.87YR | 3.21 | 0.09 | 1.56Y | 7.15 | 0.83 | 1.8 |
| Example 7 | 736 | No Maximum | 3.21RP | 3.84 | 0.25 | 1.66Y | 7.35 | 0.32 | 1.7 |
| Example 8 | 741 | No Maximum | 9.26YR | 3.45 | 0.24 | 1.86Y | 7.56 | 1.08 | 1.5 |
| Example 9 | 670 | No Maximum | 1.11Y | 3.32 | 0.33 | 1.86Y | 7.66 | 1.10 | 1.4 |
| Comparative Example 1 | 405 | No Maximum | 5.44PB | 1.40 | 2.19 | 4.78Y | 8.16 | 2.10 | 1.6 |
| Comparative Example 2 | 741 | No Maximum | 8.23YR | 5.10 | 0.04 | 2.51Y | 7.88 | 0.86 | 2.0 |
| Comparative Example 3 | No maximum | No Maximum | 6.74B | 5.73 | 0.79 | 1.94Y | 5.89 | 2.53 | 2.1 |
| Comparative Example 4 | — | — | 5.38B | 4.13 | 0.69 | 1.94Y | 6.28 | 2.21 | 4.5 |
| Comparative Example 5 | 492 | No Maximum | 5.78B | 4.58 | 0.72 | 2.10Y | 6.12 | 2.36 | 1.6 |
| Comparative Example 6 | 488 | No Maximum | 5.56B | 4.61 | 0.68 | 2.01Y | 6.07 | 2.31 | 1.6 |
| Comparative Example 7 | 485 | No Maximum | 6.52B | 2.53 | 4.01 | 4.17Y | 8.06 | 1.20 | 1.5 |
| Comparative Example 8 | 485 | No Maximum | 6.52B | 2.53 | 4.01 | 4.17Y | 8.06 | 1.20 | 1.5 |

[1])Values within parentheses represent amounts of incorporation (parts by mass).
[2])(Refractive index of filler) − (Refractive index of polymer of monomer)

TABLE 4

| Example No. | Model tooth | Filling site | Color tone adaptability (Low-chromaticity model tooth) A system | Color tone adaptability (High-chromaticity model tooth) A system | Color tone adaptability (Low-chromaticity model tooth) B system | Color tone adaptability (High-chromaticity model tooth) B system |
|---|---|---|---|---|---|---|
| Example 1 | Lower right #6 | Center of occlusal surface | B2 | B2 | A2 | A2 |
| Example 2 | Lower right #6 | Center of occlusal surface | A1 | A2 | B1 | B2 |
| Example 3 | Lower right #6 | Center of occlusal surface | A1 | A1 | B1 | B1 |
| Example 4 | Upper right #3 | Tooth cervix | A1 | A1 | B1 | B1 |
| Example 5 | Lower right #6 | Center of occlusal surface | A2 | A2 | B1 | B1 |
| Example 6 | Lower right #6 | Center of occlusal surface | A1 | A1 | B1 | B1 |
| Example 7 | Lower right #6 | Center of occlusal surface | A1 | A2 | B1 | B1 |
| Example 8 | Lower right #6 | Center of occlusal surface | A1 | A2 | B1 | B2 |

TABLE 4-continued

| Example No. | Model tooth | Filling site | Color tone adaptability (Low-chromaticity model tooth) A system | Color tone adaptability (High-chromaticity model tooth) A system | Color tone adaptability (Low-chromaticity model tooth) B system | Color tone adaptability (High-chromaticity model tooth) B system |
|---|---|---|---|---|---|---|
| Example 9 | Lower right #6 | Center of occlusal surface | A1 | A1 | B1 | B1 |
| Comparative Example 1 | Lower right #6 | Center of occlusal surface | D | D | D | D |
| Comparative Example 2 | Lower right #6 | Center of occlusal surface | C | C | C | C |
| Comparative Example 3 | Lower right #6 | Center of occlusal surface | D | D | D | D |
| Comparative Example 4 | Lower right #6 | Center of occlusal surface | C | B2 | D | D |
| Comparative Example 5 | Lower right #6 | Center of occlusal surface | D | D | D | D |
| Comparative Example 6 | Lower right #6 | Center of occlusal surface | D | D | D | D |
| Comparative Example 7 | Upper right #1 | Incisal part | A2 | A2 | A2 | A2 |
| Comparative Example 8 | Lower right #6 | Center of occlusal surface | D | D | C | C |

As is understood from the results of Examples 1 to 9, it is understood that when the requirements defined in the present invention are satisfied, the curable composition exhibits a colored light on a black background and has satisfactory color tone adaptability, and the change in color tone over time of a cured article thus obtainable is small.

As is understood from the results of Comparative Examples 1 to 3 and 5 to 8, it is understood that when the requirements defined in the present invention are not satisfied, the curable composition does not exhibit a colored light on a black background (Comparative Example 1: the average particle size of the spherical filler is 80 nm; Comparative Example 3: the shape of the filler is irregular), the colored light is weak (Comparative Example 2: the proportion of particles within the range of average particle size±5% of the spherical filler is 87%), the colored light is bluish (Comparative Examples 5 and 6: refractive index of the polymer>refractive index of the spherical filler, Comparative Examples 7 and 8: average particle size of the spherical filler<230 nm), and all of the curable compositions exhibited inferior adaptability to the color tone of the dentinal surface.

As is understood from the results of Comparative Example 4, for the curable composition having the color tone adjusted by adding a pigment (color tone compatible to the A system of high-chromaticity model tooth), the spectral reflectance was measured on a black background and a white background using a color difference meter (manufactured by Tokyo Denshoku Co., Ltd., "TC-1800 MKII"), and it was observed that the curable composition exhibited spectral reflection characteristics according to the pigment added, both on a black background and on a white background. The color tone adaptability to a color tone that was compatible to the A system of a high-chromaticity model tooth, was satisfactory; however, the color tone adaptability to other model teeth was low. Furthermore, significant changes in color tone over time were observed.

The invention claimed is:

1. A curable composition comprising:
   a polymerizable monomer component (A);
   a spherical filler (B) having an average particle size in the range of 260 nm to 1,000 nm; and
   a polymerization initiator (C),
   wherein when measurement is made for the curable composition in a state of having formed a cured article having a thickness of 1 mm, using a color difference meter, the cured article of the curable composition gives out a colored light having a value (V) of less than 5, a chroma (C) of 0.05 or greater, and a hue (H) of 0 RP or greater and less than 10 RP, 0 R or greater and less than 10 R, 0 YR or greater and less than 10 YR, or 0 Y or greater and less than 10 Y in the colorimetric values according to the Munsell Color System on a black background, and having a value (V) of 6 or greater and a chroma (C) of less than 2 in the colorimetric values according to the Munsell Color System on a white background,
   wherein 90% or more of the individual particles that constitute the spherical filler (B) exist in the range of the average particle size plus or minus 5%, and
   wherein the polymerizable monomer component (A) and the spherical filler (B) are respectively selected so as to satisfy condition (X1) represented by the following Formulas (1) and (2):

$$nP < nF \qquad (1)$$

$$nF - nP > 0.002 \qquad (2);$$

wherein nP represents the refractive index at 25° C. of a polymer obtained by polymerizing the polymerizable monomer component (A); and nF represents the refractive index at 25° C. of the spherical filler (B).

2. The curable composition according to claim 1, wherein the curable composition includes a plurality of kinds of (meth)acrylic compounds as the polymerizable monomer component (A), and the refractive index (25° C.) of the polymerizable monomer component (A) is in the range of 1.38 to 1.55.

3. The curable composition according to claim 1, wherein the spherical filler (B) is spherical silica-titanium group oxide-based composite oxide particles, and the refractive index (25° C.) of the particles is in the range of 1.45 to 1.58.

4. A dental filling restorative material consisting of the curable composition according to claim 1.

5. The dental filling restorative material according to claim 4, wherein the average particle size of the spherical filler (B) is in the range of 260 nm to 500 nm, and the filling restorative material is for use in restoration of a cavity in which dentine is positioned at the surface of a deep part.

6. The dental filling restorative material according to claim 5, wherein the average particle size of the spherical filler (B) is in the range of 260 nm to 350 nm, and the dentine has a red-brownish color tone part.

* * * * *

UNITED STATES PATENT AND TRADEMARK OFFICE
CERTIFICATE OF CORRECTION

PATENT NO. : 10,758,457 B2
APPLICATION NO. : 15/769234
DATED : September 1, 2020
INVENTOR(S) : Hironobu Akizumi et al.

It is certified that error appears in the above-identified patent and that said Letters Patent is hereby corrected as shown below:

In the Claims

Claim 1, Column 26, Line 61, the symbol ">" should read -- $\geq$ --.

Signed and Sealed this
Fifth Day of January, 2021

Andrei Iancu
*Director of the United States Patent and Trademark Office*